United States Patent
Orza

(10) Patent No.: US 10,850,246 B2
(45) Date of Patent: Dec. 1, 2020

(54) METHOD FOR PREPARING PH DEPENDENT ULTRA SMALL POLYMERIC NANOPARTICLES FOR TOPICAL AND/OR TRANSDERMAL DELIVERY

(71) Applicant: Anamaria Orza, Atlanta, GA (US)

(72) Inventor: Anamaria Orza, Atlanta, GA (US)

(73) Assignee: IndagoMed, LLC, Atlanta, GA (US)

( * ) Notice: Subject to any disclaimer, the term of this patent is extended or adjusted under 35 U.S.C. 154(b) by 0 days.

(21) Appl. No.: 15/356,701

(22) Filed: Nov. 21, 2016

(65) Prior Publication Data
US 2017/0182472 A1 Jun. 29, 2017

(51) Int. Cl.
| | |
|---|---|
| *A61K 9/14* | (2006.01) |
| *A61K 8/11* | (2006.01) |
| *A61K 9/51* | (2006.01) |
| *A61K 9/54* | (2006.01) |
| *A61K 9/58* | (2006.01) |
| *A61K 9/64* | (2006.01) |
| *B01J 13/00* | (2006.01) |
| *A61K 9/127* | (2006.01) |
| *A61K 47/69* | (2017.01) |
| *B01J 13/06* | (2006.01) |
| *B01J 13/22* | (2006.01) |
| *A61K 8/73* | (2006.01) |
| *A61K 8/85* | (2006.01) |
| *A61K 8/68* | (2006.01) |
| *A61K 8/02* | (2006.01) |
| *A61Q 19/00* | (2006.01) |
| *A61Q 19/08* | (2006.01) |

(52) U.S. Cl.
CPC ........... *B01J 13/006* (2013.01); *A61K 8/0266* (2013.01); *A61K 8/11* (2013.01); *A61K 8/68* (2013.01); *A61K 8/736* (2013.01); *A61K 8/85* (2013.01); *A61K 9/1271* (2013.01); *A61K 9/5123* (2013.01); *A61K 9/5153* (2013.01); *A61K 9/5161* (2013.01); *A61K 47/6939* (2017.08); *A61Q 19/00* (2013.01); *B01J 13/06* (2013.01); *B01J 13/22* (2013.01); *A61K 2800/56* (2013.01); *A61Q 19/08* (2013.01)

(58) Field of Classification Search
CPC .......... B01J 13/006; B01J 13/06; B01J 13/22; A61K 8/11; A61K 47/6939; A61K 8/736; A61K 9/5123; A61K 9/5153; A61K 8/85; A61K 8/68; A61K 8/0266; A61K 9/5161; A61K 9/1271; A61K 2800/56; A61Q 19/00; A61Q 19/08
See application file for complete search history.

(56) References Cited

U.S. PATENT DOCUMENTS

2003/0235619 A1* 12/2003 Allen ............... A61K 9/127
424/490
2006/0083781 A1* 4/2006 Shastri ............ A61K 9/0009
424/450

* cited by examiner

Primary Examiner — Gollamudi S Kishore

(57) ABSTRACT

The invention provides a new method for preparing ultra-small polymeric-lipidic delivery nanoparticles (USDNs) that were synthesized by a nanoprecipitation method followed by a layer-by-layer nanodeposition. The USDNs particle size can be controlled between 5-25 nm and provides loading capacities of 22.12% to 72.08%. Moreover, the USDNs platform provides pH controlled drug release, within a terminal release ratio of 68% at pH 5.0 and almost no release to pH of 7.5. Furthermore, based on their small sizes (5-25 nm) and unique composition, the USDNs penetrates the skin strata efficiently, release the payload at the target site as topical or transdermal treatment of a variety of skin disorders. Additionally the USDNs system can be used to treat and diagnoses other crucial diseases (Cancer, Alzheimer, etc) can be combined with various micro-needles or needles free array technologies for special application.

11 Claims, No Drawings

METHOD FOR PREPARING PH DEPENDENT ULTRA SMALL POLYMERIC NANOPARTICLES FOR TOPICAL AND/OR TRANSDERMAL DELIVERY

FIELD

The field of the present invention is in the area of therapeutics and nanotechnology. The invention relates to a new, pH dependent, ultra small biodegradable polymeric-lipid nanoparticles (USNDs), their synthesis method and their application as topical and/or transdermal delivery systems in a wide range of fields, from cosmetics to medical therapies and to diagnosis.

BACKGROUND

Topical and/or transdermal delivery of therapeutic compounds provides advantages over the oral administration routes by offering pain free self-administration of therapeutics with controlled drug release; and therefore, eliminating the frequent oral dosage, the active ingredient concentration fluctuation in the plasma, as well as, the drug half-life inconveniences; and confer; enhanced patient compliances by avoiding the hepatic first pass metabolism, and the gastro intestinal tract of the poorly bioavailable drugs.

The transdermal systems are generally inexpensive, are highly accepted by the patients, and have an outgoing increase of the market, that worth $12.7 billion dollars in 2005, with an increase expectancy of USD 1,504.7 Billion by 2020; thus, growing at a CAGR of 7.5% from 2015 to 2020.[1]

Currently, the US market offers more than 20 transdermal and 10 topical/dermal products (TDP). The marketed transdermal products are in the form of a patch with few variations, such as: gels and sprays, and are indicated for a wide range of therapies, [2] such as: products associated with the treatment of arthritis pain, neuropathy and muscle pain, neurologic disorders, etc.

For instance, TDP-containing drugs such as methylphenidate was introduced on the market in 2006 for the treatment of the attention-deficit hyperactivity disorder. In 2007, Rotigotine was introduced for Parkinson's disease and Rivastigmine for dementia. [3,4,5] Few other examples of FDA approved transdermal drugs are: the local anesthetic, Synera® that utilizes a controlled heat to enhance its penetration to the skin and Diclofenac, that was approved to be delivered as a topical product for the treatment of osteoarthritis joint pain. Their skin penetration mechanism is based on the slow adsorption and transportation through the skin barrier to the dermis with small amounts being released in the systematic circulation.

The drawback of the developed transdermal systems is that they contain various penetration enhancers in the delivery formulation or device and they frequently cause skin irritation and other skin dermatitis, and allergic side effects. Therefore, there is a need to develop new smart and non-toxic systems that can transdermally administrate the medicinal agent by avoiding the side effects.

The present invention addresses this need and provides additional benefits based on the discovery of an ultra small non-toxic and biodegradable nanoparticles (USDNs) that transports the therapeutics using a core-shell encapsulation method. The encapsulation process follows: $1^{st}$, encapsulating the substance between the lipid core and the biodegradable polymer shell (lipid-polymer); and $2^{nd}$, subsequently wrapping other active substance/or same around the lipid-polymer surface using an outer polymer layer. The outer layer is used both as a co-encapsulating layer and as a protective layer for blocking the active substances inside the lipid-polymer core. The USDNs particle size can be controlled between 5-23 nm and provides loading capacities of 22.12% to 72.08%, but most preferable of 30%. Moreover, the USDNs platform provides pH controlled drug release, within a terminal release ratio of 68% at pH 5.0 and almost no release to pH of 7.5

The USDNs platform can be used to treat/diagnose and broad range of dysfunctions, from skin disorders to other crucial diseases as: Cancer, Alzheimer, etc., and can be combined with various micro-needles or needles-free array technologies for special application. The USDNs platform can be also used in the cosmetic industry.

SUMMARY OF INVENTION

One major limitation for the transdermal system application is given by the skin stratum corneum that acts as a protective barrier and selectively blocks high molecular weight chemicals to penetrate through it. However, low penetration rates are reported for: low molecular weight compounds (<500 Daltons) and moderate lipophilic compounds (octanol-water partition coefficient of 10-1000). Thus, various passive and active penetration methods are used to overcome this limitation.

Owing the selective nature and the complexity of the stratum corneum, there are few TDP on the market. Only 15 small drugs (including but not limited to: Estradiol, Clonidine, Estradiol and levonorgestrel, Fentanyl, Granisetron, etc) have proven a systematically delivery with relevant therapeutic rates. These drugs constitute the whole segment of this market. Additionally, there are currently a number of ongoing FDA-clinical trials related to transdermal, delivery of various drugs. To name just a few: Miscellaneous or investigational agents (Parkinson disease, intoxication, cancer), Scopolamine (for vomiting and nausia), Rotigotine (Parkinson), Rivastigmine (Alzheimer, Parkinson), Methylphenidate (attention deficit disorder), Buprenorphine (chemotherapy), Fentanyl (pain and palliative care), etc.[6] In the cosmetic industry or in various topical treatments, penetration enhancers are used to increase the penetration rate of the active compounds.[7]

Therefore, new ways to overcome the skin barrier and provide smooth cutaneous delivery of drugs and active molecules have been studied by many research groups for over three decades. Various passive and active penetration methods were used to enhance the molecules delivery. The passive penetration method uses specific enhancers or eutectic systems [8] that are added in formulations to increase the diffusion coefficient and the solubility (partition coefficient) of the molecule to be delivered. Examples of current enhancers used are: alcohols, sulfoxides, fatty acids, etc. They reduce the skin resistance by causing a temporary disorder of the stratum corneum lipid structure. [9] Recent strategies that allow increasing both the diffusion and the solubility of the delivered molecules are using nano-sized carriers [10]

Unfortunately, the passive penetration methods are not sufficient; therefore, other electrical, mechanical and energy-related techniques were applied to enhance the delivery of the aforementioned compounds. These techniques are categorized as active skin penetration enhancement methods. The active penetration involves the distortion of the stratum corneum using: (a) micro-needles arrays; [11] (b) needle free injections [12]; (c) ultrasound waves; [13] (d) electroporation; [14] or by (e) abrasion of the stratum corneum.[15]

Among these, recently, a special attention has been driven to needle-free injections based techniques, where a jet of drug penetrates the skin using a high-speed stream of fluid.[16,17,18] The efficiency of the needle free-injection to deliver the drug through the stratum corneum depends on various parameters: injection pressure, syringe orifice diameters (SOD), size of the injected molecules. When using needle free injection to deliver therapeutics, the depth of the injection jet and the dispersion pattern has a great influence on the efficiency of the delivery. Studies showed that if the SOD and the pressure is increased, the depth of the in drug penetration and the channel diameter increased, while the within dispersion decreased. Moreover, using nanoparticles in combination with the needle-free, the size of the particles it's crucial. If the nanoparticles size is increased, the puncture opening, along with the channel diameter and the desperation depth is decreasing.[13]

The aforementioned approaches (active, passive distortion of the strata) are used in order to overcome the penetration limits of some compounds. However, these approaches usually cause skin irritation, include: irritant contact dermatitis, allergic contact dermatitis, inflammation of the skin and T-cell-mediated inflammatory response to specific allergens. The irritant contact dermatitis often causes scaling and necrotic burns, while the allergic contact dermatitis cases erythema, edema and vesiculation reactions.

The penetration enhancer methods contribute to the skin irritation by changing the physiological pH of the skin: causing disruption in the stratum corneum by using delipidisation, hydration; causing adverse immunological and reactions, etc.

To overcome the irritation it is necessary to manage the device or/and the formulation composition through the entire process. Additionally, new smart delivery methods through the encapsulation of the macromolecules and the avoidance of the irritants is highly desire. Therefore, methods and ways to prevent the irritation and enhance the penetration of high molecular weight molecules it's the research focus of many scientific groups.

Breakthroughs in chemical permeation enhancement with minimum or even zero irritation show promises through the use of nanotechnology science and its delivery platforms.

Nanotechnology will pity a major role in the delivery of cutaneous medication and can be used alone or in combination with active, passive delivery techniques or with the micro-infection or needle free injections. In recent years, significant effort has been devoted towards the development of nanotechnology based carriers for the used in needle injections. Mostly, polymeric nanoparticles were tested and delivered to various sites such as: eye[19], nose[20], brain and even intestines.[21]

Topical and transdermal delivery of active components using both the passive and the active delivery can provide better treatment for various skin diseases. Moreover, for an optimum delivery, the delivery platform needs to have enough solubility in the lipid domain of the stratum corneum, while still having sufficient hydrophilic nature to allow partitioning into the skin inner layers.

The skin permeation barrier is challenging but new exciting avenues using nanoatechnology for the delivery of active compounds into the skin strata (topical delivery) and/or into the systematic circulation (transdermal delivery) are promising and they are worth being explored.[22,23]

Nanotechnology along with its unique nanocarriers have been intensively studies to diagnose and treat various medical problems. Nano topical and transdermal delivery to various skin diseases, show superior advantages such as: (a) controlled drug release; (b) protection against drug degradation; (c) offer high stability of drugs; (d) targeted internalization by their functionalization with targeted peptides and anti-bodies; (e) accumulation of the drug in high concentrations at specific sites; (f) co-delivery of two or more drugs in the same platform; (g) avoided plasma level drug peaks; (h) and enhanced efficiency and patient compliance.

Nanosized delivery has been widely explored to enhance the delivery of active agents through the stratum corneum. To date, polymeric nanoparticles (both natural and synthetic), lipid nanoparticles, liposomes and various nanoemulsions have been widely reported as topical formulations to enhance the penetration of the active components through the startum corneum.[24] The nano sized platform skin penetration pathways mechanism, for both topical and transdermal delivery occurs: (a) via intercellular/intracellular routs (stratum corneum) and via partitioning/diffusion part; and (b) through the appendageal pathway.

However, small irritations have been reported by the use of liposomal and some polymeric delivery systems. The topical and transdermal delivery system used to transport the desired components through the strata, needs to have enough solubility in the lipid domain of the stratum corneum, while still having sufficient hydrophilic nature to allow partitioning into the skin inner layers. Additionally, it needs to have certain sizes and shapes to allow a high efficient internalization and clearance and advanced biodegradability rates. Comprising all these properties in one-nano delivery stems is challenging.

The research is now focused on developing a new generation of delivery system that could offer optimized: composition, structural properties, size; and controlled tunable properties. Moreover, the further optimized delivery platform must ultimate improves the therapeutic potential and offer non-toxicity, non-irritation and fast system clearance.

Classes of delivery platforms such as: layer-by-layer hybrid lipid-polymeric nanoparticles, core-shell metal polymeric nanoparticles, are an example of those.[25] They combine the benefits of liposomes and polymeric nanoparticles and have shown increased internalization of venous drugs,[26,27] nucleic acids,[28,29] and others to the desired site.

Beside the composition of the delivery system, their size and shape can dramatically alter the performance of the skin penetration, transdermal transport and bio-distribution[30] It has been reported that ultra small nanoparticles around 2-5 nm in size have a faster and higher penetration rate[31] and are extruded by the kidney[32,33] However, there is a much debate concerning the perfect size of the nanoparticles as delivery systems; the size should be chosen depending on the application and the platform in question. For instance, the delivery of therapeutics to the brain is particularly difficult due to the brain bather; however, ultra small nanoparticles (<50 nm) show efficient accumulation in the brain.[34,35,36]

In the present invention overcome the obstacles presented above by relating a new ultra small delivery system that penetrates the stratum corneum in an efficient way and releases the drug to the targeted site, without providing skin irritation.

The invention provides a method to synthesize an ultra small hybrid biodegradable platform of a size between 3 nm to 25 nm, but most preferable of 5 nm; that: (1) has the ability to introduce targeting functionalities on its surface, such as: delivery enhancers, from a class of cell penetrating peptide enhancers or a combination of those, (transactivator of transcription (TAT) protein from the HIV virus, meganin, penetratin, TD-1, and SPACE-peptide, IMT-P8; Institute of Microbial Technology-Peptide 8 (IMT-P8), antennapedia, transportan and polyarginin); (2) as well as co-encapsulate two or more therapeutic agents (wherein said, therapeutic agent is selected from a class of: an anti-aging end anti-wrinkle agent, a drug or a group of drugs or active biological molecules with psoriasis and rosacea or any other skin disorder, a chemeotherapeutic agent, an antibiotic, antiseptic or antiviral agent); (3) and release them to the targeted sites in a percentages within 22.12% to 72.08%, but most preferable of 30% in a controlled pH manner (at pH 5.0 and almost no release to pH of 7.4 or up.). Due to its size and composition and ability to encapsulate two or more therapeutic components (biological active for a wide range of disorders) under the same particle, this platform can be used as topical and transdermal delivery to treat and/or detect various dysfunction.

The USDNs transdermal drug delivery and its method of penetrating with no side effects the stratum corneum and it's method of controlling the drug release in accordance with the present invention have one or more of the following advantages:

(1) The currently developed USDNs nanocarrier can encapsulate two or more drugs, that are quickly released in a pH controlled manner and the speed of the release is determinate by the properties of the outer shell and inner shell (such as hydrophilicity, hydrophobicity and crystallinity) of polymers. There is no hybrid ultra small (5 nm) polymer delivery system that is capable to coencapsulate and control the drug release speed in a variety of skin disorders.

(2) The present invention provides a ultra small and biodegradable nanoparticle that has encapsulated a combination of desired active ingredients and has the ability to control the release of the drug from topical application or from a micro-needle or needle-free carrier.

(3) The present invention, under acidic conditions (pH=5.5-6.5) is leaking out the drugs with a 38.65% and 27.81% release ratio in 12 h, and a terminal release ratio of was determined to be at 60.91% and respectively, 52.14%. in 90 h. However, under neutrally condition (pH 7.4), almost no drugs were released (4.2%). The invention can be applied but not limited to treat disease that requires long-term treatments.

(4) By using the present invention a variety of transdermal drug delivery therapies (including topical formulations, patches or needle free injections), that release desired dosages of drug, can be developed by encapsulation of specific drug and their release can be pH-controlled by choosing the right polymer. Therefore, in accordance with the present invention, minimally invasive control release is achieved with reduced side effects of the drug and highly efficient treatment effect.

(5) The USDNs can be self-administrated and provides pain free therapy and as chosen, can enter into the targeted tissue side or circulating into the whole body. The USDNs platform can be used to neat/diagnose and broad range of dysfunctions, from skin disorders to other crucial diseases as: Cancer, Alzheimer, etc., and can be combined with various micro-needles or needles-free array technologies for special application. The USDNs platform can be also used in the cosmetic industry (6) Based on its composition the USDNs will degrade or/and dissolve in the human body by providing no side effects and toxicity.

DESCRIPTION OF THE INVENTION

In certain embodiments, this disclosure relates to a layer by layer ultra small hybrid biodegradable and non-toxic nanoparticle (USDNs) comprised of a lipid core, followed by a two subsequently shell of a middle biodegradable polymer layer entrapped in an outer natural polymer. These nanoparticles can be encapsulated with at least one active substance, wherein; the active substance can comprise but is not limited to the following group of therapeutic active substances: an anti-aging and anti-wrinkle agent, a drug or a group of drugs or active biological molecules with psoriasis and rosacea or any other skin disorder, a chemeotherapeutic agent, an antibiotic, anitispetic or antiviral agent, wherein, the said USDNs surface contain delivery enhancers molecules (TAT, IMT-P8, etc) and can be also conjugated with any bio-active ligand for targeted drug delivery, wherein said, the USDNs is used as a topical or/and transdermal delivery, wherein said, the USDNs penetrates the skin strata efficiently, release the active substances at the target site as topical or transdermal treatment for a variety of skin disorders, wherein, the USDNs system can be also used to treat and diagnoses other crucial diseases (Cancer, Alzheimer, etc) and can be combined with various micro-needles or needles-free array technologies for special application.

Given the potential benefits of both the size and composition, the present invention relates a facile synthesis method of a biodegradable lipid-polymer nanoparticle having a size less then 25 nm, preferable less than 10 nm and most preferable of 5 nm. Active molecules can be inserted into the nanoparticles, including more than one active molecule such as therapeutic agents and diagnosis agents. The previously reported sizes of hybrid layer-by-layer nanoparticles were from 50 nm to grater than 200 nm.

The particles has a hybrid polymer-lipid composition, where the lipid is from a class of phospholipids, wherein, the preferred lipid is 1,2-Distearoyl-snglycero-3-phosphoethanolamine and the polymer is from a class of biodegradable polymers and natural polymers, wherein, the preferred polymer is Carboxylic acid-terminated poly(lactic-co-glycolic acid) (PLGACOOH; 50:50 ratio) and chitosan. The USDNs is such designed to have enough solubility in the lipid domain of the stratum corneum, while still having sufficient hydrophilic nature to allow partitioning into the skin inner layers for an optimum delivery. The USDNs lipid core has a hydrophobic nature that enables to encapsulate and deliver high molecular weight or/and hydrophobic drugs [37], which have poor penetration properties through the sin barrier. The lipid core is then surrounded in a biodegradable polymer shell (that wraps the core and co-encapsulates more drags) and subsequently covered by outer chitosan-TAT layer. Herein, the TAT peptide is used as a penetration enhancer, chitosan was used both to stabilize the hybrid platform and to co-encapsulate active molecules.

The ultra small nanoparticles (5 nm) stability in water, phosphate buffer saline (PBS at pH-8), and under physiological conditions (in fetal bovine serum) was determined by DLS. The analysis was conducted for 24 hours and slight change of the hydrodynamic size were observed suggesting that presence of highly strength media and the physiological condition do not change the surface properties of the nanoparticle significantly. The system such made is stable in relevant physiological conditions and can co-encapsulate higher quantities of active substance, biological molecules, etc.

The co-encapsulation of multiple active molecules is processed as follows: (1) into the core and (2) onto the lipid layer (between the lipid layer and the chitosan shell) into one platform, wherein, the desired intrinsic properties and integrity of the platform and of the active compounds present into the platform is not affected. The USDNs platform and the encapsulated molecules offer independent and associative properties to each individual component of die system. Moreover, the loading of the drugs has little effect of the size and disparity of the USDNs.

Drugs@USDNs appears d with similar average particle size and the encapsulated drugs are related to the psoriasis treatment such as: (1) efalizumab; and (2) the interleukin-12/23 (IL-12/23) monoclonal antibody, ustekinumab, where, the CD11a chain of LFA-1 inhibitor and cell adhesion, efalizumab, was encapsulated in the core and the antibody between the shells. The zeta potential of the Drugs@USDNs was −4.2 mV, which increased to 12.6 and 15.0 mV after surface modification with TAT. The presence of the TAT amino groups endowed the Drugs@USDNs platform with positive charge.

The antibody, ustekinumab is presently used as an injectable and require repeated injections and some patients experience a loss of therapeutic effect. Moreover, efalizumab was withdrawn from the market because of serious side effects. Therefore, using the present invention platform co-encapsulation, the side effects and the toxicity was highly diminished or overcome. Moreover, the system allows lower quantity of drugs to be delivered, thus, resulting in lower or even zero toxicity and high delivery and treatment performance.

Drug Loading and pH-Mediated Release:

Two important factors that determine the efficiency of the Nanocarrier are the loading capacity and the release behavior. The drugs loaded onto the platform are two drugs with activity in the treatment of psoriasis: efalizumab and ustekinumab where, the CM11a chain of LFA-1 inhibitor and cell adhesion, efalizumab was encapsulated in the core and the antibody, ustekinumab, between the core and chitosan shells.

The co-delivery platform, Drugs@USDNs of 5 nm and respectively 10 nm, has a drug loading capacity of about 300-500 µ/mg but most preferable of 400 µg/mg. Moreover, since the release behavior of the platform is pH-mediated, the platform was exposed in PBS under various pH conditions varying from pH=[7.4-5.0]. The pH-mediated release has an important impact on the platform's application. In various skin diseases, the pH of the stratum corneum and epidermis, dermis, etc is deregulated by the activity of the pH dependent enzymes, which regulates skin cornification desquamation and homeostasis of the barrier function. In patients suffering from epidermal photogene's such psoriasis, the skin surface pH has been reported to be between pH=[6-6.5].[38] Therefore, the herein platform, under acidic conditions (pH=5.5-6.5) is leaking out the drugs with a 38.65% and 27.81% release ratio in 12 h, and a terminal release ratio of was determined to be at 60.91% and respectively, 52.14% in 90 h. However, under neutrally condition (pH 7.4), almost no drugs were released (4.2%). The chitosan layer is responsible for the first release of the drug, the denaturation of its amino acids in acidic conditions leads to the destabilization of the layer and the release of the drug, while, the lipid core degrade as well in strong acidic to lower acidic condition.

In conclusion, the patent relates a new method to synthesize an ultra small hybrid platform that has the ability to introduce targeting functionalities on its surface as well as co-encapsulate two or more active ingredients and release them to the targeted sites in a percentages within 22.12% to 72.08% at pH 5.0 and almost no release to pH 7.4 or up. Due to its size and composition, this platform has a wide range of applications, including topical and transdermal delivery, brain targeted delivery, tumor penetration, vaccination for the treatment of various diseases.

In Vitro Delivery of Drugs@USDNs:

Herein, the disclosed fabrication methods of the USDNs provide the ability to functionalize and stabilize its surface, and provide tailored characteristics that improve the delivery and treatment/diagnosis. Many active ingredients can be encapsulated into the nanoparticles and delivered to the payload site. An active ingredient can be a substance that is administrated into the body especially for a desired application, and has a biological effect on the organism. The USDNs can be loaded with both hydrophilic and hydrophobic active ingredients.

Based on its small sizes and composition, the USDNs have a high capacity to carry active molecules into the cells. Moreover, the internalization is enhanced by the presence of TAT molecules on its surface. The internalization efficiency was monitored in-vitro by incubating the platform with meduloblastoma cells and using Using florescence microscopy to confirm its internalization. In a typically study, 5 µM of Drugs@USDNs was functionalized with FITC and then incubated with meduloblastoma cells for 1 h at 37° C. The uptake of the Drugs@USDNs-FITC (contain TAT) was compared with Drugs@USDNs-FITC (without TAT). Considerable higher florescence was observed for the when cells were treated with Drugs@USDNs-FITC (contain TAT), which indicates that TAT increases the internalization capacity of the platform.

Skin Penetrating Properties of LMT-P8 In Vivo:

Given the results demonstrating that Drugs@USDNs is capable of transporting the medication inside the cells, a further investigation of the ability to penetrate the stratum corneum and enter into epidermis was performed; so that, it could be used as carrier for topical and/or transdermal drug delivery. After 2 h the skin section treated with FITC-Drugs@USDNs, the green florescence was observed in epidermis with diffusion in the dermal tissue, which suggests the ability of the platform to penetrate the stratum corenum efficiently and accumulate into the epidermis in a short period of time. Additionally, lower green florescence was observed in the hair follicles.

EXPERIMENTS

Synthesis of the pH Dependent Ultra Small Polymeric Nanoparticles (Drugs@USDNs).

Disolution of Chitosan 1% in HCl Acid

Chitosan solution (0.1%) was prepared by dissolving 1 g of chitosan in 90 ml of distilled water containing 20 in of HCl and by mixing the followed solution at 60° C. for 24 h.

Preparation of TAT-Chitosan

First, TAT-chitosan conjugation was performed as follows: 1 ml of 1% chitosan in 1% HCl solution containing by adjusting the pH-6 were mixed with 200 mM EDAC and 200 mM NHSS at room temperature for 5 min. After, 5 mg of HIV-1 Tat peptide was added to the chitosan solution and stirred for 4 h at room temperature. Next, 1 mg of tris(2-carboxy-ethyl)phosphine hydrochloride was added and the solution was then left undisturbed for 30 min. The sample was then purified using centrifugation.

Layer-by-Layer Synthesis of the USDNs

The preparation of the USDNs was preformed using the following nanoprecipitation process such as: Step 1. At pH=8, the carboxylic acid-terminated polylactic-co-glycolic acid) (1 mg mL-1), previously dissolved in acetonitrile, was precipitated and stabilized with a solution of 1,2-Distearoyl-snglycero-3-phosphoethanolamine-N-[methoxy(polyethylene glycol)] dissolved in Tris-HCl. Step.2. Further, 2 ml TAT-chitosan was added into the solution and the reaction was continued for another 8 h. The resulting nanoparticles were filtrated using a 100 kDa Amicon centrifugal filter and the size were measure by Transmission electron microscopy (TEM). The TEM grids were prepared by depositing a 30 µl of the as prepared particles on a 100 meshes cupper grid. The resulted nanoparticle have a size of 5 nm. In order to obtain larger sizes of nanoparticles, of 5-25 nm, the concentration of TAT-chitosan was vary between 1-5 ml, wherein the most preferable are ultra small sizes of 5 nm.

The nanoparticles are highly stabile both in psychological conditions and water and their stability was analyzed in: phosphate buffer saline (PBS), fetal bovine serum (FBS) and 10 mM Tris-HCl a: pH 8 for 2 weeks. Such as, 2 mg ml$^{-1}$ of nanoparticles were added to 2 ml of PBS/FBS/Water and DLS measurements were performed twice a day until day 14.

Drugs or Active Substances Loading into the USDNs Platform

The CD11a chain of LFA-1 inhibitor and cell adhesion, efalizumab, and the interleukin-12/23 (IL-12/23) monoclonal antibody, ustekinumab, were loaded into the USDNs platform by physically encapsulation. The efalizumab was dissolved into the PLGA phase and the synthesis was processed as described above at Step.1. Further, ustekinumab was added into the nanoprecipitate and then Step 2 of the reaction was followed. (as described above at Layer-by-Layer Synthesis of the USDNs). Then, thw resulted nanoparticles were purified by using a 100 KDa MWCO Amicon centrifugal filters to remove the excess of the encapsulated drugs and other unreacted row materials. The quantity of the drug loaded was quantified by using PerkinElmer Series 200 high performance liquid chromatography (HPLC) system using a C18 analytical column (Brownlee) with a mobile phase of 50:50 water to acetonitrile and a detection wavelength of 230 nm. Moreover, the quantity of drug released and retained at various pH and time was assessed.

Toxicity of Nanoparticles USDNs Platform

Cytotoxicity of the nanoparticles was examined using 3-(4,5-dimethylthiazol-2-yl)-2,5-iphenyltetrazolium bromide (MTT) assay with two different cell lines, i.e., HEK293 human embryonic kidney cell, HeLa and D556human brain tumor medulloblastoma cell. The cells were maintained as an adherent culture and grown as a monolayer in a humidified incubator (95% air, 5% CO2) at 37° C. in a cell culture flask containing medium supplemented with 1% penicillin-streptomycin and 10% FBS. Cells were detached and seeded in 96-well flat-bottom microplates at 4000 cells per well. After 24 h recovery at 37° C., the medium was replaced with 100 µl medium containing nanoparticles (USDNs or Drug@USDNs) at various concentrations (12.5-400 µg/ml). For the control cell sample, a fresh medium without nanoparticles was added. After 24 h of incubation at 37° C., 10 µl of MTT solution (5 mg/ml) was added into each well following a 4 h incubation period. After removing the culture media, the precipitated formazan was then dissolved in 10% SDS in 0.01M HCl. Finally, a micro plate reader (Biotech Synergy2) was used to measure the absorption of all samples (n=6 per group) at 570 nm. Cell viability was determined by comparing the absorptions of cells incubated with and those without nanoparticles.

CITATION LIST

[1] http://www.marketsandmarkets.com/PressReleases/drug-delivery-technologies.asp. Accessed on Nov. 16, 2016.

[2] Prausnitz M R, Mitragotri S, Langer R. Current status and future potential of transdermal drug delivery. Nat Rev Drug Discov. 2004; 3(2):115-124.

[3] Prausnitz M R., Langer R. Transdermal drug delivery. Nat Biotech. 2008; 26(11):1261-1268.

[4] Micromedex® 1.0 (Healthcare Series) Thomson Reuters. [Accessed 17 Nov. 2016]. www.thornsonhc.com/home.

[5] 202. Rx List. [Accessed 17 Nov. 2016]. www.rxlist.com/script/main/hp.asp.

[6] ClinicalTrials.gov. [Accessed 17 Nov. 2016]. www.clinicaltrials.gov. Alvarez-Roman R, Naik A, Kalia Y N, Guy R H, Fessi H. Skin penetration and distribution of polymeric nanoparticles. J Control Release. 2004; 99:53-62.

[7] Moser K, Kriwet K., Naik A, Kalia Y N, Guy R H. Passive skin penetration enhancement and its quantification in vitro. Eur J Pharm Biopharm. 2001; 52:103-112.

[8] Barry B W. Penetration enhancer classification. In: Smith E W, Maibach H I, editors. Percutaneous penetration enhancers. 2. Taylor and Francis; New York, USA: 2006. pp. 3-16.

[9] Alvarez-Roman R, Naik A, Kalia Y N, Guy R H, Fessi H. Enhancement of topical delivery from biodegradable nanoparticles. Pharm Res. 2004; 21:1818-1825.

[10] Cormier M, Johnson B, Ameri M, Nyam K, Libiran L, Zhang D D, Daddona P. Transdermal delivery of desmopressin using a coated microneedle array patch system. J Control Release. 2004; 97:503-511.

[11] Park C H, Tijing L D, Kim C S, Lee K M. Needle-free transdermal delivery using PLGA nanoparticles: effect of particle size, injection pressure and syringe orifice diameter, Colloids Surf B Biointerfaces. 2014 Nov. 1; 123: 710-5.

[12] Alvarez-Roman R, Merino G, Y N, Naik A, Guy R H. Skin permeability enhancement by low frequency sonophoresis: Lipid extraction and transport pathways. J Pharm Sci. 2003; 92:1138-1146

[13] Mori K, Hasegawa T, Sato S, Sugibayashi K. Effect of electric field on the enhanced skin permeation of drugs by electroporation. J Control Release. 2003; 90:171-179

[14] Akomeah F K, Martin G P, Middle A G, Brown M B. Effect of abrasion induced by a rotating brush on the skin permeation of solutes with varying physicochemical properties. Eur J Pharm Biopharm. 2008; 68:724-734

[15] J. Schramm, S. Mitragotri, Transdermal drug delivery by jet injectors: energetics of jet formation and penetration, Pharm. Res. 19 (2002) 1673-1679.

[16] S. Mitragotri, Current status and future prospects of needle-fiveliquidjetinjec-tors, Nat. Rev. Drug Discov. 5 (2006) 543-548.

[17] Y. Michinaka, S. Mitragotri, Delivery of polymeric particles into skin using needle-free liquid jet injectors, J. Control. Release 153 (2011) 249-254.

[18] R. Cavalli, M. R. Gasco, P. Chetoni, S. Burgalassi, M. F. Saettone, Solid lipid nanoparticles (SLN) as ocular delivery system for tobramycin, Int. J. Pharm. 238 (2002) 241-245.

[19] R. Fernandez-Urrusuno, P. Calvo, C. Remuñsn-López, J. Vila-Jato, M. José Alonso, Enhancement of nasal absorption of insulin using chitosan nanoparticles, Pharm. Res. 16 (1999) 1576 1581.

[20] R. Ghirardelli, F. Bonasoro, C. Porta, D. Cremaschi, Identification of particular epithelial areas and cells that transport polypeptide-coated nanoparticles in the nasal respiratory mucosa of the rabbit, Biochim. Biophys. Acta (BBA)—Biomembr. 1416 (1999) 39-47.

[21] Hadgraft J, Guy R H. Feasibility assessment in topical and transdermal delivery: Mathematical models and in vitro 22 Tee R W, Shenoy D B, Sheel R. Chapter 2: Micellar nanoparticles: applications for topical and passive transdermal drug delivery. Kulkarni V S, editor. Handbook of non-invasive drug delivery systems. Elsevier Inc; Burlington, Mass., USA: 2010. pp. 37-58.pp. 37-58

23 Guterres S S, Alves M P, Pohlmann A R. Polymeric nanoparticles, nanospheres and nanocapsules, for cutaneous applications. Drug Target Insights. 2007; 2:147-157.

24 L. Zhang, J. M. Chan, F. X. Gu, J. W. Rhee, A. Z. Wang, A. F. Radovic-Moreno, F. Alexis, R. Langer and O. C. Farokhzad, ACS Nano, 2008, 2, 1696-1702.

25 J. M. Chan, L. Zhang, K. P. Yuet, G. Liao, J. W. Rhee, It Langer and O. C. Farokhzad, Biomaterials, 2009, 30, 1627-1634.

26 S. Aryal, C. M. J. Hu, V. Fu and L. Zhang, J. Mater. Chem., 2012, 22, 994-999.

27 W. Hasan, K. Chu, A. Gullapalli, S. S. Dunn, E. M. Enlow, J. C. Luft, S. M. Tian, M. E. Napier, P. D. Pohlhaus, J. P. Rolland and J. M. DeSimone, Nano Lett., 2012, 12, 287-292.

28 19 X. F. Su, J. Fricke, D. G. Kavanagh and D. J. Irvine, Mol. Pharm., 2011, 8, 774-787.

29 J. W. Yoo, E. Chambers and S. Mitragotri, Curr. Pharm. Des., 2010, 16, 2298-2307.

30 Huo S, Chen S, Gong N, Liu J, Li X, Zhao Y, Liang X. T. Bioconjug Chem. 2016 Ultra-Small Gold Nanoparticles Behavior in Vivo Modulated by Surface PEG Grafting.

31 F. Alexis, E. Pridgen, L. K. Molnar and O. C. Farokhzad, Mol. Pharm., 2008, 5, 505-515.

32 23 E. Blanco, H. Shen and M. Ferrari, Nat. Biotechnol., 2015, 33, 941-951.

33 M. Bramini, D. Ye, A. Hallerbach, M. N. Raghnaill, A. Salvati, C. Aberg and K. A. Dawson, ACS Nano, 2014, 8, 4304-4112.

34 27 D. H. Jo, J. H. Kim, T. G. Lee and J. H. Kim, Nanomedicine, 2015, 11, 1603-1611.

35 28 W. Rao, H. Wang, J. Han, S. Zhao, J. Dumbleton, P. Agarwal, W. Zhang, G. Zhao, J. Yu, D. L. Zynger, X. Lu and X. He, ACS Nano, 2015, 9, 5725-5740.

36 B. S. Pattni, V. V. Chupin and V. P. Torchilin, Chem. Rev., 2015, 115, 10938-10966.

37 Li Ye,1 Chenvhi Lv,1 George Man,2 Shunpeng Song,1 Peter M. Elias,2 and Mao-Qiang Man2, Abnormal Epidermal Bather Recovery in Uninvolved Skin supports the Notion of an Epidermal Pathogenesis of Psoriasis J Invest Dermatol. 2014 November; 134(11): 2843-2846.

The invention claimed is:

1. A method for making a hybrid, biodegradable, non-toxic phospholipid polymer nanoparticle, comprising
   i) nanoprecipitating a biodegradable polymer, wherein the biodegradable polymer is selected from the group consisting of polylactic (PLA) and polvglycolic (PGA) polymers; poly lactic-co-glycolic acid copolymers (PLGA): diblock copolymers containing a functional poly(ethylene glycol) (PEG) and PLGA (PEG-PLGA); PEG-PLA diblocks: triblock copolymers containing PEG and PLGA; polymers and copolymers of polycaprolactones polymer; polycaprolactones-(poly(acrylic acid) (PAA) copolymer; (2-ethyl-2-oxazoline) (PEtOz) poly(N-isopropylacrylamide; poly(N,N-dimethylamino-2-ethyl methacrylate) linked to a hydrophobic polycaprolactones segment: poly(alkyl cyanoacrylates); poly(ortho esters); poly(anhydrides) of poly (sebacic acid), poly(adipic acid) or poly(terphthalic acid); poly(amides); polyester amides) and poly(phosphoesters)
   ii. stabilizing said biodegradable polymer with a phospholipid-polymer layer to produce a stabilized nanoprecipitate,
   iii) adding a natural polymer, wherein the natural polymer is a protein-based polymer or polysaccharide,
   iv) reacting said stabilized nanoprecipitate and said natural polymer,
   v) adding at least one active substance, wherein said at least one active substance is added:
      a) to the stabilized nanoprecipitate produced in step ii) before reacting said stabilized nanoprecipitate and said natural polymer, to encapsulate the active substance between a polymer shell and an outer shell comprising a natural polymer, and/or
      b) to the biodegradable polymer of step i) to produce a polymer-active substance mixture before stabilizing the polymer-active substance mixture with a phospholipid layer in step ii), which results in a lipid core encapsulated nanoprecipitate having at least one active substance entrapped inside the phospholipid core,
   vi) filtering any resulting nanoparticles,
   wherein said hybrid, biodegradable, non-toxic phospholipid-polymer nanoparticle, comprises
      a) a phospholipid core comprising a biodegradable polymer and a phospholipid,
      b) a polymer shell encapsulating the phospholipid core,
      c) an outer shell comprising a natural polymer, and
      d) at least one active substance which is encapsulated inside the phospholipid core, and/or between the polymer shell and the outer shell comprising the natural polymer,
   and wherein said hybrid, biodegradable, non-toxic lipid polymer nanoparticle is 3 nm-25 nm in size.

2. A method for increasing skin penetration of a topically or transdermally administered active substance, comprising encapsulating said active substance in the hybrid, biodegradable, non-toxic lipid-polymer nanoparticle made according to claim 1 and topically administering said hybrid, biodegradable, non-toxic lipid-polymer nanoparticle to a patient in need of such treatment.

3. The method according to claim 1, wherein the polylactic-co-glycolic acid polymers are selected from the group consisting of aliphatic polyesters PGA, PLA, and PLGA; the PLGA copolymer is a PLGA and PEG copolymer; and/or the poly(amides) are selected from the group consisting of poly(amino acids), poly(γ-glutamic acid) and poly(L-lysine).

4. The method according to claim 1, wherein said protein-based polymer is selected from the group consisting of collagen, albumin, and gelatin and/or said polysaccharide is selected from the group consisting of agarose, alginate, carrageenan, hyaluronic acid (HA), dextran, chitosan, and cyclodextrins.

5. The method according to claim 1, wherein at least two active substances are added, wherein at least one active substance is encapsulated in the lipid core and at least one active substance is encapsulated between the biodegradable polymer shell and the outer shell comprising a natural polymer shell, and wherein one active substance is hydrophobic and one active substance is hydrophilic.

6. The method according to claim 5, wherein the outer shell comprising the natural polymer further comprises groups for the conjugation of targeting bioactive molecules and/or delivery enhancers.

7. The method according to claim 6, wherein the targeting bioactive molecules are bio-affinitive ligands that recognize a specific cell.

8. The method according to claim 6, wherein the delivery enhancers are bio-affinitive cell penetrating peptides selected from the group consisting of a transactivator of transcription (TAT) protein from the HIV virus, meganin, penetratin, TD-1, SPACE-peptide, IMT-P8, antennapedia, transportan and polyarginine.

9. The method according to claim 1, wherein said active substance is selected from the group consisting of an anti-aging agent, an anti-wrinkle agent, a drug for treating skin disorders, a chemotherapeutic agent, a diagnostic agent, an antibiotic, an antiseptic agent and an antiviral agent.

10. The method according to claim 1, wherein the lipid core comprises carboxylic acid-terminated poly(lactic-co-glycolic acid) and 1,2-Distearoyl-snglycero-3-phosphoethanolamine, and the biodegradable polymer shell comprises polyethylene glycol and the natural polymer is chitosan.

11. A hybrid, biodegradable, non-toxic phospholipid-polymer nanoparticle, comprising
   a) a lipid core comprising a biodegradable polymer and a phospholipid,
   b) a polymer shell encapsulating the phospholipid core,
   c) an outer shell comprising a natural polymer, and
   d) at least one active substance which is encapsulated inside the lipid core, and/or between the polymer shell and the outer shell comprising the natural polymer,
   wherein said hybrid, biodegradable, non-toxic lipid-polymer nanoparticle is 3 nm-25 nm in size, and
   wherein said hybrid, biodegradable, non-toxic lipid-polymer nanoparticle is produced by a method comprising:
   i) nanoprecipitating a biodegradable polymer, wherein the polymer is selected from the group consisting of polylactic (PLA) and polyglycolic (PGA) polymers; poly lactic-co-glycolic acid copolymers (PLGA); diblock copolymers containing a functional poly(ethylene glycol) (PEG) and PLGA (PEG-PLGA); PEG-PLA diblocks; triblock copolymers containing PEG and PLGA; polymers and copolymers of polycaprolactones polymer; polycaprolactones-(poly(acrylic acid) (PAA) copolymer; (2-ethyl-2-oxazoline) (PEtOz); poly(N-isopropylacrylamid; poly(N,N-dimethylamino-2-ethyl methacrylate) linked to a hydrophobic polycaprolactones segment; poly(alkyl cyanoacrylates); poly(ortho esters); poly(anhydrides) of poly(sebacic acid), poly (adipic acid) or poly(terphthalic acid); poly(amides); polyester amides) and poly(phosphoesters)
   ii. stabilizing said biodegradable polymer with a phospholipid polymer layer to produce a stabilized nanoprecipitate,
   iii) adding a natural polymer, wherein the natural polymer is a protein-based polymer or polysaccharide,
   iv) reacting said stabilized nanoprecipitate and said natural polymer,
   v) adding at least one active substance, wherein said at least one active substance is added:
   a) to the stabilized nanoprecipitate produced in step ii) before reacting said stabilized nanoprecipitate and said natural polymer, to encapsulate the active substance between a polymer shell and an outer shell comprising a natural polymer, and/or
   b) to the biodegradable polymer of step i) to produce a polymer-active substance mixture before stabilizing the polymer-active substance mixture with a phospholipid layer in step ii), which results in a lipid core encapsulated nanoprecipitate having at least one active substance entrapped inside the lipid core, and
   vi) filtering any resulting nanoparticles.

* * * * *